(12) United States Patent
Sprague et al.

(10) Patent No.: US 6,979,402 B1
(45) Date of Patent: Dec. 27, 2005

(54) MINIATURE ACTUAL MOVING BED ASSEMBLY

(75) Inventors: Robert T. Sprague, Crystal Lake, IL (US); Gavin P. Towler, Barrington, IL (US); Anil R. Oroskar, Oakbrook, IL (US)

(73) Assignee: UOP LLC, Des Plaines, IL (US)

( * ) Notice: Subject to any disclaimer, the term of this patent is extended or adjusted under 35 U.S.C. 154(b) by 164 days.

(21) Appl. No.: 10/741,666

(22) Filed: Dec. 19, 2003

(51) Int. Cl.[7] ............................................. B01D 15/08
(52) U.S. Cl. .................... 210/198.2; 210/264; 210/267; 210/657; 210/659; 210/676
(58) Field of Search ................ 210/656, 659, 210/676, 198.2, 264, 267, 657

(56) References Cited

U.S. PATENT DOCUMENTS

| | | | |
|---|---|---|---|
| 2,985,589 A | 5/1961 | Broughton et al. ............ 210/34 |
| 3,040,777 A | 6/1962 | Carson et al. ......... 137/625.15 |
| 3,201,491 A | 8/1965 | Stine et al. ................. 260/676 |
| 4,157,267 A | 6/1979 | Odawara et al. .......... 127/46 A |
| 4,182,633 A | 1/1980 | Ishikawa et al. .......... 127/46 A |
| 4,313,015 A | 1/1982 | Broughton .................. 585/828 |
| 4,319,929 A | 3/1982 | Fickel ........................ 127/46.2 |
| 4,402,832 A | 9/1983 | Gerhold ....................... 210/659 |
| 4,409,033 A | 10/1983 | LeRoy ...................... 127/46.2 |
| 6,280,623 B1 * | 8/2001 | Ma ............................. 210/264 |
| 6,576,137 B1 * | 6/2003 | Ma ............................. 210/657 |

OTHER PUBLICATIONS

Dr. Ing. Herbert Knauer GmbH, CSEP® C9 Series Simulated Moving Bed Chromatography Systems Manual, Dec. 2000.

* cited by examiner

Primary Examiner—Ernest G. Therkorn
(74) Attorney, Agent, or Firm—John G. Tolomei; Frank S. Molinaro; Arthur E. Gooding

(57) ABSTRACT

An apparatus is presented for separating chemicals using adsorption separation methods. The apparatus uses a plurality of adsorption units holding adsorbent, where the adsorption units positioned in a cylindrical spool, are serially connected and the spool is rotated to shift the relative position of the feeds and drawoffs to the apparatus.

19 Claims, 8 Drawing Sheets

MINIATURE ACTUAL MOVING BED ASSEMBLY

FIELD OF THE INVENTION

The invention relates to an apparatus useful for contacting beds of solid materials with a fluid. The invention is directly related to an apparatus for use in contacting a flowing fluid stream with an absorbent in an adsorptive separation process. The invention is specifically directed to a system with a plurality of contacting beds with distribution and collection ports placed at several intermediate points between neighboring beds, allowing for the addition or withdrawal of a fluid stream at these points, and the beds are moved countercurrent to the flow of the fluid.

BACKGROUND OF THE INVENTION

The separation of various substances through selective adsorption is an important process for producing pure substances. However, this generally is a batch process, but with the development of simulated moving bed (SMB) technology, the adsorption separation process can be operated on a continuous basis. For simulated moving bed technology, the process uses a multiport rotary valve to redirect flow lines in the process. The simulation of a moving adsorbent bed is described in U.S. Pat. No. 2,985,589 (Broughton et al.). In accomplishing this simulation, it is necessary to connect a feed stream to a series of beds in sequence, first to bed no. 1, then to bed no. 2, and so forth for numerous beds, the number of beds often being between 12 and 24. These beds may be considered to be portions of a single large bed whose movement is simulated. Each time the feed stream destination is changed, it is also necessary to change the destinations (or origins) of at least three other streams, which may be streams entering the beds, such as the feed stream, or leaving the beds. The moving bed simulation may be simply described as dividing the bed into series of fixed beds and moving the points of introducing and withdrawing liquid streams past the series of fixed beds instead of moving the beds past the introduction and withdrawal points. A rotary valve used in the Broughton process may be described as accomplishing the simultaneous interconnection of two separate groups of conduits.

There are many different process requirements in moving bed simulation processes, resulting in different flow schemes and thus variations in rotary valve arrangement. For example, in addition to the four basic streams described in Broughton (U.S. Pat. No. 2,985,589), it may be desirable to utilize one or more streams to purge, or flush, a pipeline or pipelines. A flush stream is used to prevent undesirable mixing of components. The flush substance is chosen to be one which is not undesirable for mixing with either main stream, that being purged or that which enters the pipeline after flushing is completed. U.S. Pat. No. 3,201,491 (Stine et al.) may be consulted for information on flushing lines as applied to the process of Broughton (U.S. Pat. No. 2,985,589). It may be desirable to pass fluid through a bed or beds in the reverse direction from normal flow. This is commonly known as backflushing, a subject treated in U.S. Pat. No. 4,319,929 (Fickel). Other applications for various arrangements of multiport rotary disc valves may be seen in U.S. Pat. No. 4,313,015 (Broughton); U.S. Pat. No. 4,157,267 (Odawara et al.); U.S. Pat. No. 4,182,633 (Ishikawa et al.); and U.S. Pat. No. 4,409,033 (LeRoy).

While the multiport rotary disc valve of Carson (U.S. Pat. No. 3,040,777) provided a satisfactory valve design for the simultaneous interconnection of two independent groups of conduits such that each conduit of the first group could be brought into individual communication with every conduit of the second group, it is not suitable when three groups of conduits must be simultaneously interconnected in the same manner. Upon reference to Broughton (U.S. Pat. No. 2,985,589), it can be seen that there are only two groups of conduits which need to be interconnected when the arrangement of the drawing of that patent is utilized. One group consists of the conduits which provide the flows entering and leaving the simulated moving bed adsorbent system, that is, the flows which are switched among the beds, such as the feed stream. A second group consists of the conduits associated with the individual beds, that is, which supply and remove fluid from the beds, one conduit being connected between each two beds. It is to be noted that each conduit of the second group serves that dual function of supply and removal, so that it is unnecessary to provide conduits for supplying fluid separate from those for removing fluid.

When it is necessary to simultaneously interconnect conduits of three different groups of conduits in accordance with a previously determined cycle, the apparatus of the present invention may be used. An example of process involving three conduit groups may be found in U.S. Pat. No. 4,402,832 (Gerhold), which is described below. As mentioned above, it is highly desirable to use a single device to do so, thereby avoiding the obvious problems associated with numerous separate valves which must be simultaneously actuated.

One of the issues associated with simulated moving bed technology and rotary valves is the need for cross-over lines to make the appropriate connections when the rotary valve shifts the source of the feed inlets and the drawoff outlets relative to the bed. The cross-over lines often need to be long and create back mixing problems.

With the development of complex specialty chemicals and the need for high purity, there is a need for improved separation methods and apparatuses to obtain high purity specialty chemicals.

SUMMARY OF THE INVENTION

The invention provides a miniature moving bed apparatus for the contacting of a solid adsorbent with a liquid mixture. The solid adsorbent selectively adsorbs a component of the liquid mixture to separate that component from the mixture. The apparatus comprises a generally cylindrical spool having adsorbent bed channels defined therein for holding a solid adsorbent. The apparatus further comprises a bottom plate assembly affixed to the spool and having channels defined therein which connect pairs of adsorbent bed channels and allows for fluid to flow from one adsorbent bed to another adsorbent bed. A pair of adsorbent beds is defined as an adsorbent unit for purposes of this invention. The apparatus further comprises a stator plate assembly having cross-over channels defined therein, and where the cross-over channels provide fluid communication between pairs of adsorbent units. The stator plate assembly further includes connections to net flow lines for the inflow of a desorbent and a feedstream, and the outflow of an extract and raffinate stream. The apparatus also includes a means for rotating the spool to move the adsorbent beds in a direction that is generally counter-current to the flow of the liquid.

Other objects, advantages and applications of the present invention will become apparent to those skilled in the art from the following detailed description.

DETAILED DESCRIPTION OF THE INVENTION

Figure 1:
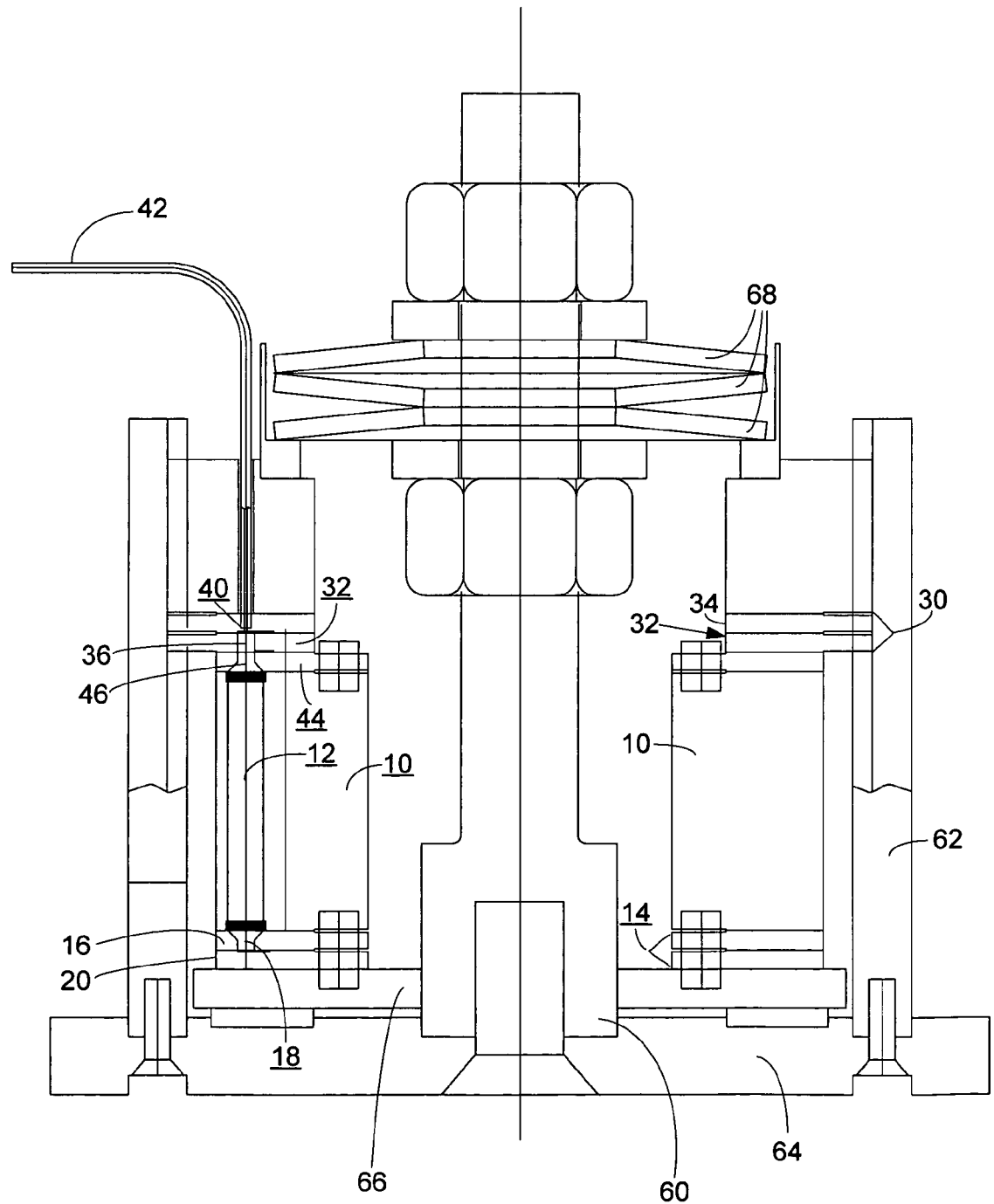
FIG. 1 is a diagram of the apparatus.

The purification and recovery of small amounts of high value, low volume materials is currently done by doing many sequential batch HPLC runs to obtain a desired level of high purity specialty chemicals. The present invention provides a continuous, and relatively low cost apparatus that can be used for separation and purification of small amounts of specialty chemicals.

Adsorptive separation processes preferably include the sequential performance of three basic steps. First, the adsorbent must be brought into contact with a feed stream comprising the particular compounds to be collected at adsorption-promoting conditions. This adsorption step should continue for a time sufficient to allow the adsorbent to collect a near equilibrium amount of the preferentially adsorbed compounds. The second basic step is the contacting of the adsorbent while it is bearing both the preferentially and non-preferentially adsorbed compounds with a material which displaces the latter from the adsorbent. The second step is performed in a manner which results in the adsorbent and the interstitial void spaces between adsorbent particles containing significant quantities of only the preferentially adsorbed feed component and the material used to displace the non-preferentially adsorbed compounds. The third basic step of the adsorptive separation process is the desorption of the preferentially adsorbed compounds, and is performed by contacting the adsorbent with a desorbent stream. The desorbent stream contains a chemical compound capable of displacing or desorbing the preferentially adsorbed compounds from the adsorbent to thereby release these compounds and prepare the adsorbent for another adsorption step. For a large scale system, it is not practicable to move the adsorption units, and then the process entails using a complex piping system to continuously reroute the feeds and drawoffs to the adsorption units. This is referred to as a simulated moving bed, or SMB, system. In a small scale system, it is convenient, and results in a simplification of the piping, to move a series of adsorption units relative to the feeds and drawoffs for the adsorption-separation system, or an actual moving bed (AMB) apparatus. This is a countercurrent chromatographic process, where the fluid phase is driven by a pressure gradient to flow in one direction, and the solid adsorbent is moved continuously past the inlet and outlet net flow ports in a direction opposite to the fluid flow. In the AMB the solid adsorbent is moved in units of adsorbent beds.

A preferred utilization of the present apparatus is a process in which the rotation of a spool holding adsorbent beds containing selective adsorptive material is performed to obtain the effects of the countercurrent flow of the unit of solid material and various entering fluid streams such as the feed and desorbent streams. This spool rotation moves the adsorbent beds and shifts the positions of the adsorbent beds relative to the inlet and drawoff streams.

Figure 2:
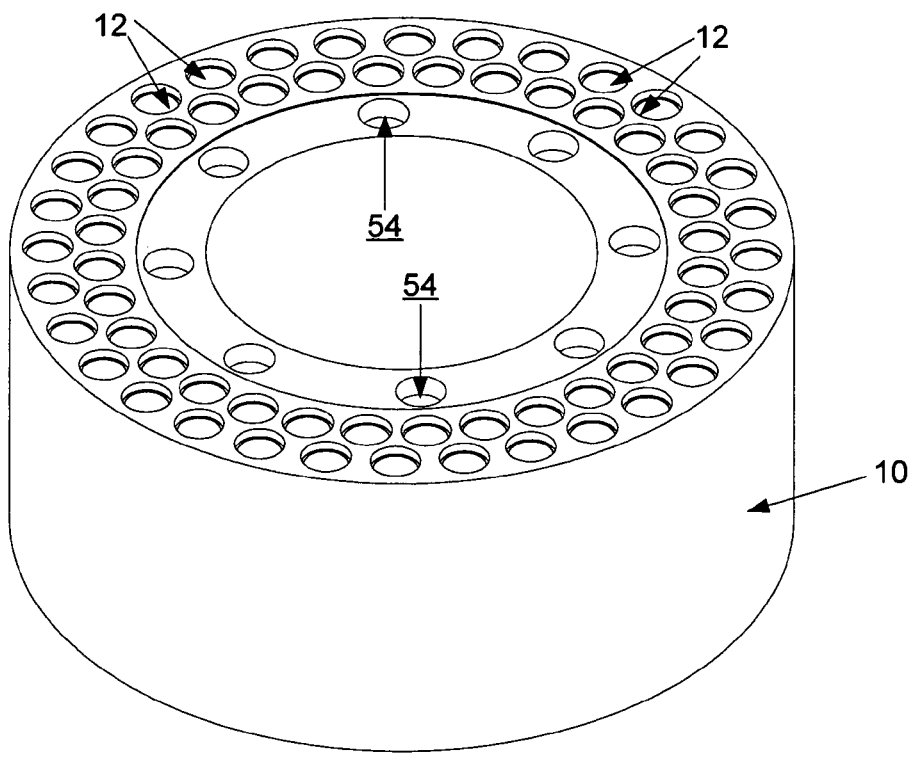
FIG. 2 is a diagram of the spool showing the openings for the adsorbent bed channels.

A cross section of the present invention is shown in FIG. 1, and is an actual moving bed apparatus for separating components from a mixture. The moving bed comprises a spool 10 wherein a plurality of adsorbent bed channels 12 are defined. The spool 10 has a generally cylindrical shape, and in a first embodiment the spool 10 has a toroidal shape. The adsorbent bed channels 12 are defined in the annular region. A perspective view of the spool 10 is shown in FIG. 2, showing openings for the adsorbent bed channels 12. The adsorbent bed channels 12 hold an adsorbent, providing a plurality of adsorbent beds, for selectively separating one chemical component from a mixture of chemicals.

Figure 3:
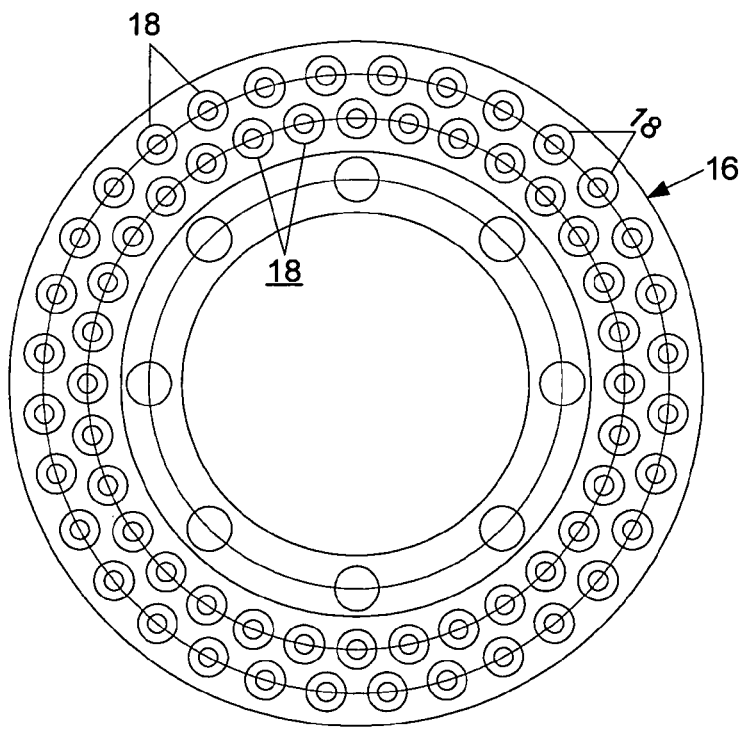
FIG. 3 is a diagram of the first bottom plate of the bottom plate assembly.
Figure 4:
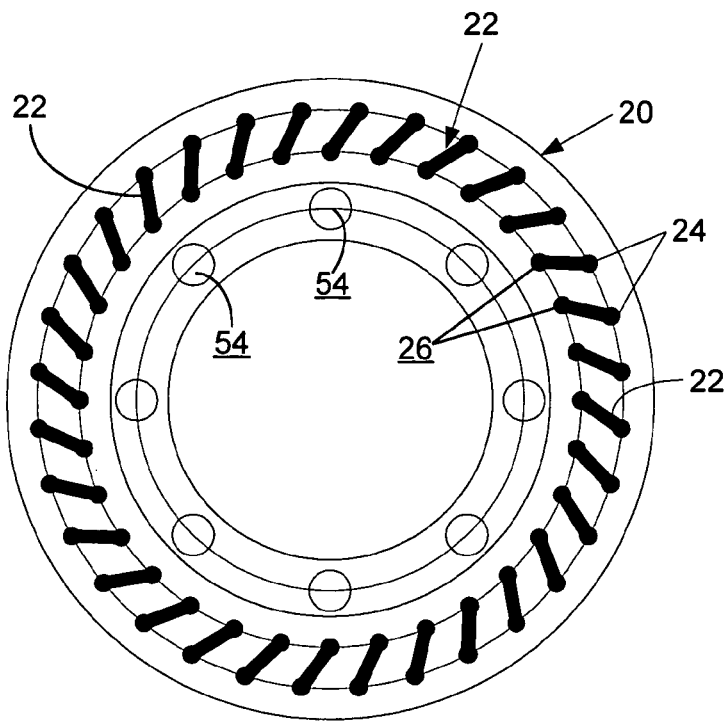
FIG. 4 is a diagram of the second bottom plate of the bottom plate assembly.

The apparatus further comprises a bottom plate assembly 14. The bottom plate assembly 14 provides for fluid communication between pairs of adsorbent bed channels 12. In one embodiment, the bottom plate assembly 14 comprises two plates, which are combined to form channels between pairs of adsorbent bed channels 12. A first bottom plate 16 is shown in FIG. 3, and has a plurality of ports 18 equal to the number of adsorbent bed channels 12, and positioned such that when the first bottom plate 16 is disposed against the bottom of the spool 10, the ports 18 are positioned over the adsorbent bed channels 12. The ports 18 extend through the first bottom plate 16 and taper from the diameter of the adsorbent bed channels 12 to a smaller diameter opening. The taper of the ports 18 is shown in FIG. 1. In this embodiment, the bottom plate assembly 14 further includes a second bottom plate 20 that is positioned against the first bottom plate 16 and is shown in FIG. 4. The second bottom plate 20 has a plurality of connecting channels 22 defined in the plate 20, wherein the connecting channels 22 each has a first end 24 and a second end 26. Each end 24, 26 of a channel 22 is positioned to align with one port 18 in the first bottom plate 16. Each channel 22 creates a fluid communication between one pair of adsorbent bed channels 12. The spool 10 in conjunction with the bottom plate assembly 14 form the equivalent of a plurality of U-shaped adsorbent units equal to one-half the number of adsorbent bed channels 12. For the purposes of simplicity in this description, an adsorption bed is a bed of adsorbent that fills one adsorbent bed channel 12, and an adsorbent unit is two adsorbent bed channels 12. It is understood that an adsorbent bed channel 12 can be divided into multiple adsorbent beds.

Figure 5:
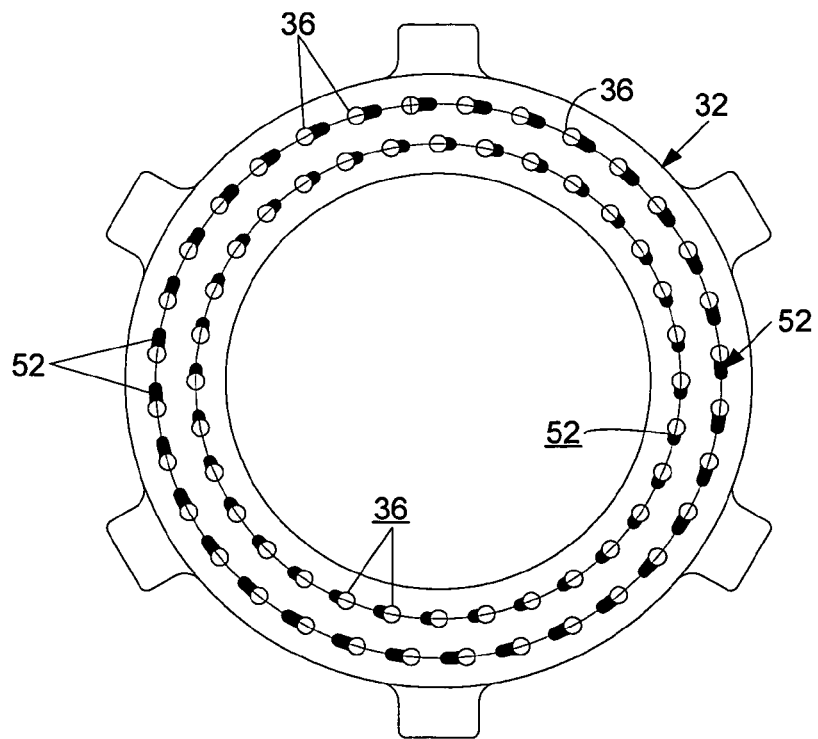
FIG. 5 is a diagram of the first stator plate.
Figure 6:
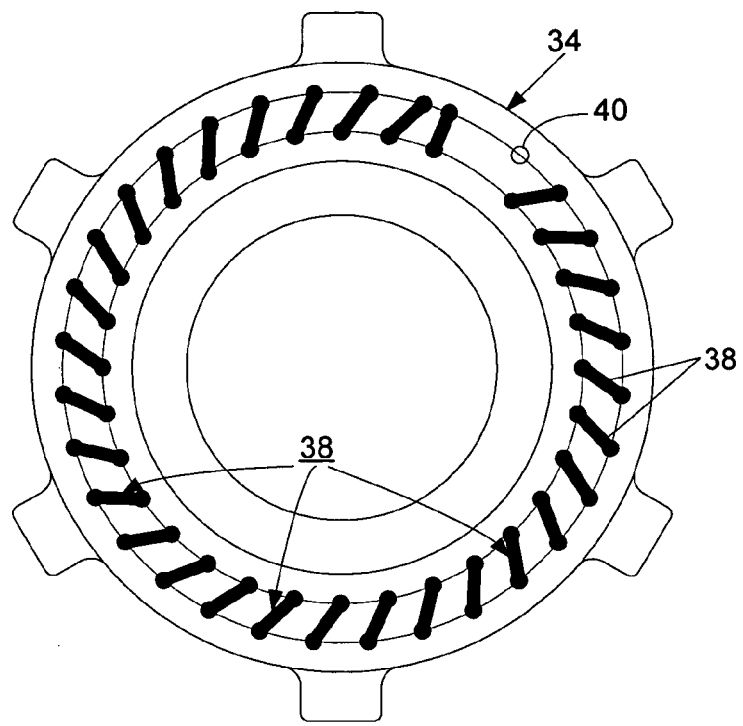
FIG. 6 is a diagram of a bottom view of the second stator plate.
Figure 7:
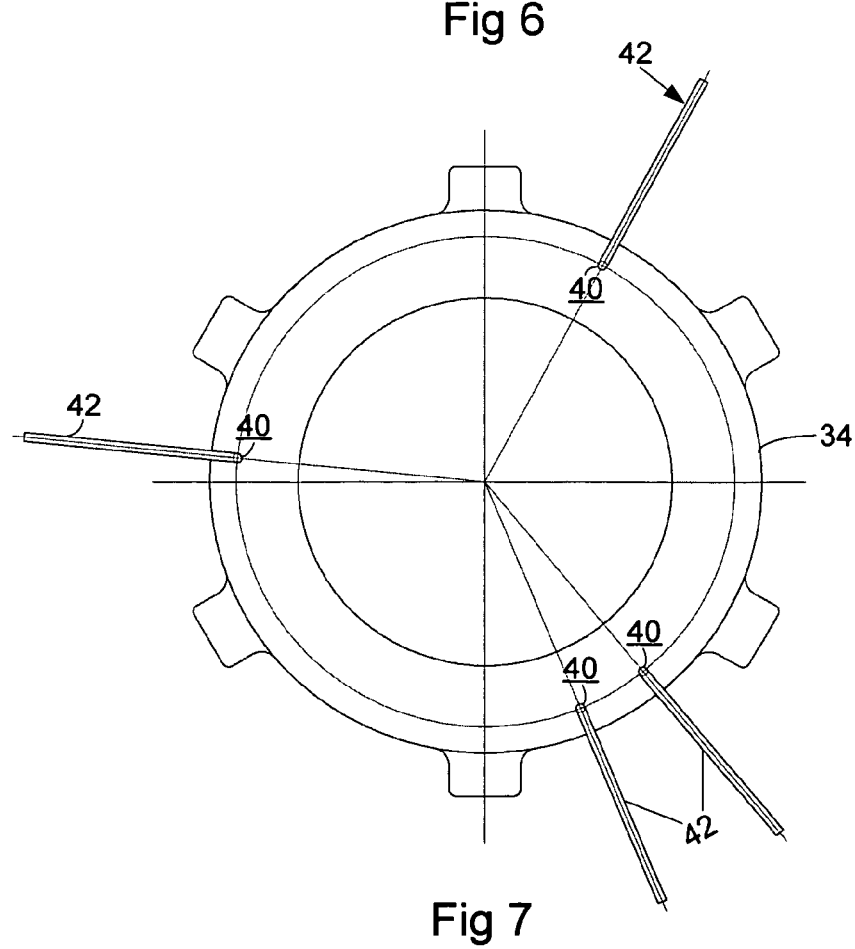
FIG. 7 is a diagram of a top view of the second stator plate with net flow lines attached.

The apparatus further includes a stator plate assembly 30. The stator plate assembly 30 provides fluid communication between neighboring adsorbent units, wherein each adsorbent unit is comprised of two adsorbent bed channels 12. The stator plate assembly 30 provides the interface between the non-moving parts of the adsorption separation apparatus and the moving bed. In one embodiment, the stator plate assembly 30 comprises two plates, a first stator plate 32 as shown in FIG. 5 and a second stator plate 34 as shown in FIG. 6. The first stator plate 32 has a plurality of ports 36 that extend through the plate 32. The number of ports 36 is equal to the number of adsorbent bed channels 12, wherein each port 36 is in periodic fluid communication with one adsorbent bed channel 12. The stator plate assembly 30 further comprises the second stator plate 34 which defines a plurality of cross-over channels 38. The cross-over channels 38 are defined on the face of the second stator plate 34 that is in contact with the first stator plate 32 and connect pairs of ports 36 in the first stator plate 32, and where each cross-over channel 38 provides fluid communication between a pair of adsorbent units, where each adsorbent unit is a pair of adsorbent bed channels 12 with adsorbent in each channel 12. The number of cross-over channels 38 is equal to one less than the number of adsorbent units, or one less than one-half of the number of ports 36. The second stator plate 34 further includes a plurality of ports 40 that pass through the plate 34. The ports 40 provide fluid communication to net flow lines 42 leaving the top of the second stator plate 34 as shown in FIG. 7. When assembled with the stator plate assembly 30, on top of the spool 10, on top of the bottom plate assembly 14, a continuous interconnection of adsorbent beds is formed. One feature of the present invention is a reduction in the size and number of crossover channels between adsorbent beds over the necessary piping for a simulated moving bed.

The combination of the connecting channels 22 connecting pairs of adsorbent bed channels 12 and the cross-over channels 38 connecting pairs of adsorbent units provides a continuous interconnected series of adsorbent beds, with connections to net flow lines. The net flow lines comprise an inlet for a desorbent, an inlet for a feedstream, an outlet for an extract stream, and an outlet for a raffinate stream. The ports 40 provide for a high pressure inlet, which is usually the desorbent inlet, and a low pressure outlet, which is usually the raffinate stream. Other ports 40 provide intermediate fluid connections to adsorbent bed channels 12 for the inlet of a feedstream and the drawoff of an extract stream. Intermediate ports 40 are ports positioned in the system between the high pressure port and the low pressure port of the system. The positioning of the intermediate ports 40 are determined by the properties of the adsorbent, the feed composition, the choice of desorbent, and the operating conditions. The material properties and operating conditions determine the relative sizes of the adsorption, purification, and desorption zones, and therefore determine the relative positioning of the intermediate ports 40. The intermediate fluid ports 40 are made through the second stator plate 34, and each connects with one of the cross-over channels 38 chosen to optimize the separation of components. By moving the adsorbent bed channels 12, the relative positions of the net flow lines to the adsorbent bed channels 12 are shifted. The adsorbent beds are moved in a countercurrent direction relative to the fluid motion.

Figure 8:
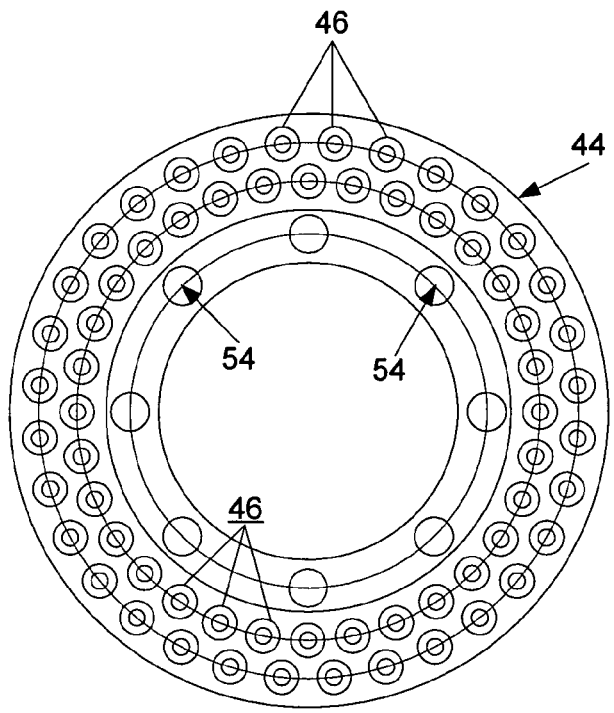
FIG. 8 is a diagram of a top plate for the top plate assembly.

In another embodiment, the invention comprises a top plate assembly 44, as shown in FIG. 8. One embodiment of the top plate assembly 44 comprises a single plate having a plurality of ports 46 which extend through the plate 44. The ports 46 taper from the diameter of the adsorbent bed channels 12 to the smaller diameter opening of the ports 36 of the first stator plate 32. The taper of the ports 46 is shown in FIG. 1.

Three items, the spool 10, the bottom plate assembly 14, and the top plate assembly 44 are held together by pressure, or can be held together by other means such as an adhesive, or mechanical attachment device such as a screw or bolt, such that when the apparatus is assembled, the three items turn as a unit. Methods for holding plate assemblies 14, 44 and the spool 10 together are well known to those skilled in the art and not described here. The spool 10, bottom plate assembly 14, and top plate assembly 44 further have means for preventing the rotation of one of the above relative to the other items. The means includes using pins, or bolts that fit in holes 54 in each of the spool 10, bottom plate assembly 14, and top plate assembly 44 to maintain a fixed orientation of the three items. An alternate method of holding the three items in a fixed orientation includes designing each of the items to have a generally toroidal shape with an inner opening, and designing the inner openings of the generally toroidal shapes to have a matching shape of a hub 60 used to turn the moving bed. One example of such a design is to make the inner openings of the spool 10, the bottom plate assembly 14, and the top plate assembly 44 with a hexagonal shape. A hub 60 having a hexagonal outer shape then mates with the inner openings and prevents movement of one of the items relative to the other items. An unlimited number of shapes and designs exist with the only requirement for the shapes and/or designs is that the hub 60, spool 10, bottom plate assembly 14, and top plate assembly 44 when assembled rotate as a single unit.

The hub 60 further provides a convenient means for attaching a means to hold the spool 10, bottom plate assembly 14, top plate assembly 44, and the stator plate assembly 30 together. In one embodiment, the hub 60 connects to a base plate 66, extends through the centers of the spool 10, bottom plate assembly 14, top plate assembly 44, and the stator plate assembly 30, and holds plate springs 68 against the top of the stator plate assembly 30. The plate springs 68 provide pressure to hold the apparatus together and to maintain a seal between the components of the apparatus. Other means for holding the apparatus are known in the art and are not discussed here.

Figure 9:
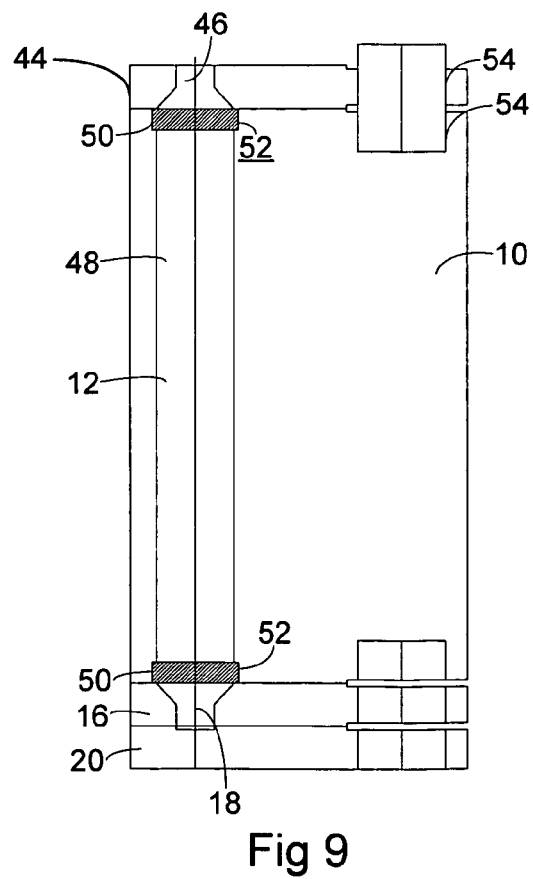
FIG. 9 is a diagram of the adsorbent bed channel with adsorbent and frits positioned to maintain the adsorbent in the channel.

The adsorbent can be placed in the adsorbent bed channels 12 by filling with a granular adsorbent, or the adsorbent can be part of an insert for convenient placement into the adsorbent bed channels 12. In one embodiment, as shown in FIG. 9, the adsorbent 48 is placed in the adsorbent bed channel 12 as a loose granular material. The adsorbent 48 is held in place by positioning frits 50 at each end of the adsorbent bed channel 12. The frits 50 can be press fitted to prevent movement and to act as a fluid distributor at the inlet end of the channel 12. Preferably, the channels 12 have a region 52 where the frits 50 are positioned, that is of greater diameter than the channel 12. The frits 50 are positioned in these regions, and held in place by the first bottom plate 16 and the top assembly plate 44, where the respective ports 18 and 46 have diameters less than the diameters of the frit regions 52. The plates 16, 44 when affixed to the spool 10 will hold the frits 50 in position. By sizing the frits 50 to have a greater diameter than the diameter of the adsorbent bed channels 12 and the ports 18, 44, slippage of the frits is prevented and facilitates the even distribution of liquid across the entrance to the adsorbent bed channel 12. It is preferred for operation of this invention that the fluid flows through the units of adsorbent in a substantially "plug flow" flow regime. That is, it is desired for the entire cross section of the adsorbent units to be evenly swept by the flowing fluid, with the fluid having a relatively uniform velocity and composition at all different points across the entire cross section of an adsorbent bed. The separational abilities and capacity of any particular adsorbent unit is in part governed by the degree of uniformity of the fluid flow through the unit since nonuniform flow can lead to back mixing, poor utilization of the adsorbent in some areas of the unit, and a dilution of the streams withdrawn from the unit with undesired materials which are also present in the process such as raffinate or desorbent materials. The frits 50 provide for smoothing of the pressure profile across the cross-section of the adsorption beds and help distribute the fluid substantially evenly.

The materials of construction of the spool is any material that is durable and rigid, and impermeable to the chemical components in the mixture to be separated. In addition, the materials of construction should not experience any preferential adsorption properties relative to the chemical components in the feed stream. One embodiment is a metal body, such as stainless steel or other corrosion resistant metal, lined with an inert polymeric material, such as TEFLON™. Another embodiment is injection molded plastic bodies with a rigid impermeable thermoset plastic.

In one embodiment, the apparatus further includes smear channels 52. As seen in FIG. 5, smear channels 52 are defined in the first stator plate 32. A smear channel 52 is a channel defined within a plate to enable fluid communication between a stationary port 36 and a rotating port 46 for a greater time and distance by having the rotating port 46 overlap the channel 52. The smear channels 52 extend from the ports 36 along the plate 32 at a uniform radius from the center of the plate 32. For a rotating system this is along a track followed by the ports 46 in the top plate assembly 44 as the adsorbent bed assembly is rotated around an axis. The smear channels 52 allow for continuous rotation of the moving beds, instead of indexing the motion of the moving beds between the ports 36 on the stator plate 32. The channels 52 are separated by a gap equal to at least the diameter of the rotating ports 46. This prevents crossover flow from one bed to a neighboring bed when the rotating bed assembly advances the adsorption bed channels 12 to have fluid communication with subsequent adsorption bed channels 12. The channels 52 are etched or machined into the plate 32 by means known in the art. The use of smear channels 52 and operation in a continuous rotation reduces pressure spikes when the connections advance from one adsorption unit to the next adsorption unit.

The smear channel 52 design is not limited to following a path lying on the same circumference as ports 36. The ports 36 may be offset from the path of the moving ports 46 to provide more compact designs, or to provide for other features, such as equal lengths of smear channels that intersect the inlet and outlet ports of the adsorbent beds, or for providing better balance of pressures and flows. In an alternate design, the smear channels can be defined in the top plate assembly 44 rather than the first stator plate 32. By disposing the smear channels on the top plate assembly 44, the ports 46 can be repositioned such that the ports 46 do not align with the ports 36 of the first stator plate 32, but are in fluid communication through the smear channels 52. This ability of using the smear channels 52 to create the fluid communication provides flexibility in design and positioning of the inlets and outlets to the adsorbent beds. The smear channels 52 extend along an arc in the direction the ports 46 in the rotating top plate 44 come from. This operation affects the movement of the opposing plate port 46 over the closed end of the channel 52 and purges the material in the smear channel, thus reducing back mixing problems.

Figure 10:
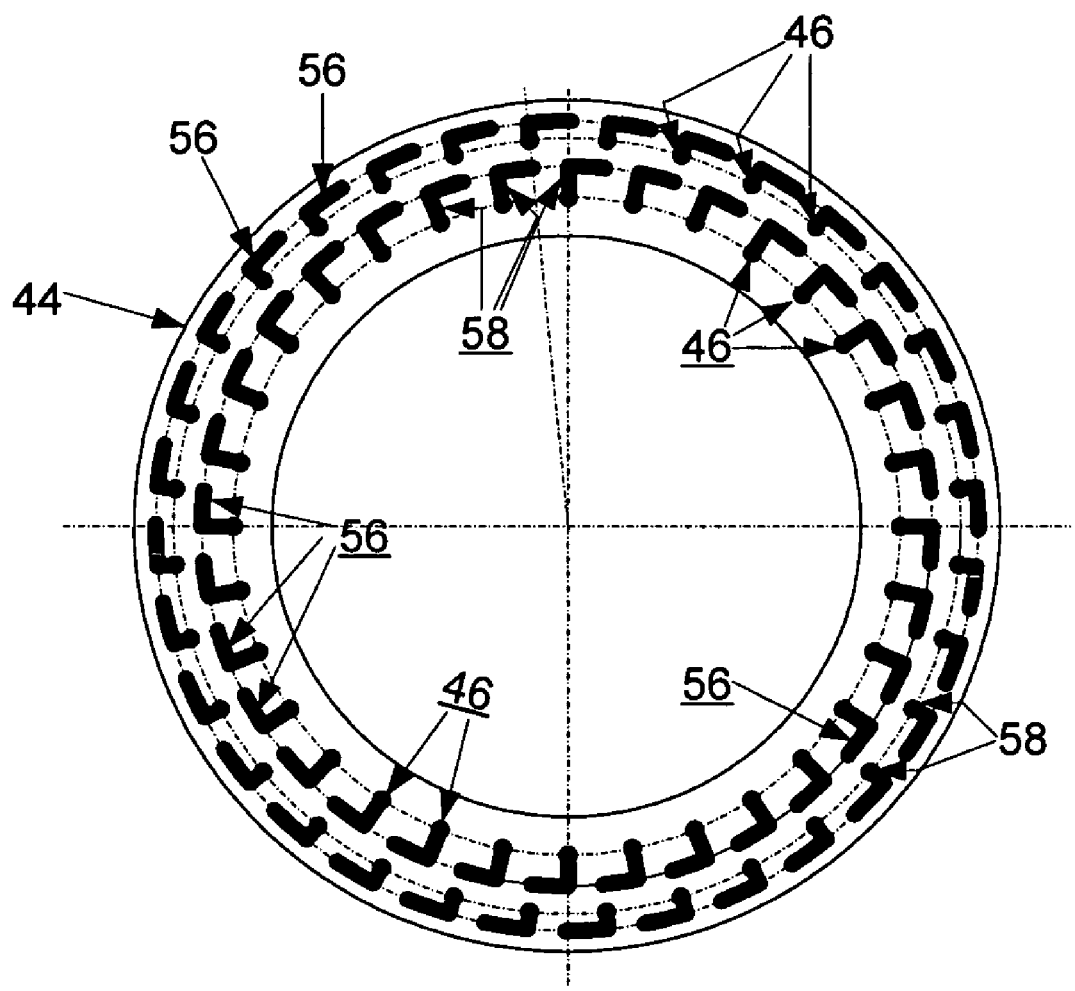
FIG. 10 is a diagram of a top plate with smear channels.

In one embodiment, the top plate assembly 44 includes smear channels 56, as shown in FIG. 10. The ports 46 through the plate 44 are positioned such that they sit over the inlets and outlets of the adsorbent beds when assembled, and a channel 58 runs from the port 46 to the portion of the smear channel 56 that is in fluid communication with the port 36 on the stator plate 32. The location of the smear channel 56 is not limited to the positional radius of the port 46, nor is the length of the smear channel limited to the arc distance between neighboring ports 46.

The inside and outside diameter of the spool 10 in the miniature moving bed device is based on the required diameters of the adsorbent bed channels 12, which are set by adsorbent bed diameter requirements, and to support the internal pressures in the adsorbent beds and the necessary forces to maintain seals between the moving top plate 44 and the first stator plate 32. Using the design shown in FIG. 10 more seal area is available at the interface between the top plate 44 and the stator plate 32. The radius at which the smear channels 56 for the inner and outer adsorbent beds can be increased relative to the radial location of the adsorbent beds, thus improving the sealing at the interface of the top plate 44 and the stator plate 32.

The miniature actual moving bed is rotated about an axis of rotation, and the ports 46 on the rotating top plate assembly 44 move and align with ports 36 on the stator plate assembly 30. When there is fluid communication between the rotating ports 46 and the stationary ports 36 flow continues through the adsorption beds. During the rotation of the adsorption beds each rotating port 46 moves from one stationary port 36 to an adjacent stationary port 36. During this rotation there is a short interruption in the fluid communication when the rotating port 46 leaves one stationary port 36 and fluid communication is reestablished when the rotating port 46 passes over a second stationary port 36, or a smear channel 52 connected to a second stationary port 36. While the sequence of connections from one adsorption bed channel 12 to the next adsorption bed channel 12 remains unchanged, the relative positions of the adsorption bed channels 12 move with respect to the net flow lines 40.

The operation can rotate the spool 10 and rotating plate assemblies 14, 44 in a step-wise manner, or in a continuous manner. When operated in a step-wise manner, the spool 10 is in one position for a predetermined period of time with the rotating ports 46 aligned with the stationary ports 36. Then the spool 10 is rotated a predetermined angle, and the rotating ports 46 are aligned with the stationary ports 36 in a different order. The flow of fluid through the adsorption beds continues in the same direction, but the movement of the spool 10 has repositioned the adsorption beds relative to the net flow lines 42. To ease the pressure pulses caused by the intermittent flow interruptions due to the interruptions in the fluid communication between the rotating ports 46 and the stationary ports 36, a smear plate is used in part of the stationary plate assembly 30. The smear plate also permits continuous rotation of the spool 10. Rotation of the spool 10 can be accomplished by any means known for rotating devices, including but not limited to direct gear drives, a chain and gear drive, a belt drive, and a direct drive shaft affixed to the hub 60.

The top plate assembly 44 slides against the stator plate assembly 30 during rotation of the adsorption beds. In addition, the top plate assembly 44 is pressed against the stator plate assembly 30 to seal the system and prevent material from leaking. The materials of construction of the plates that slide against each other are preferably comprised of a lubricious polymeric material, such as a polyfluorinated hydrocarbon. One example of a preferred material is TEFLON™. In an alternative, the plates are coated with a lubricious polymeric material.

The miniature actual moving bed assembly can be held together in a housing 62. The housing 62 provides for a base 64 to hold the hub 60, and the hub 60 and spool 10 are rotated within the housing 62.

Figure 11:
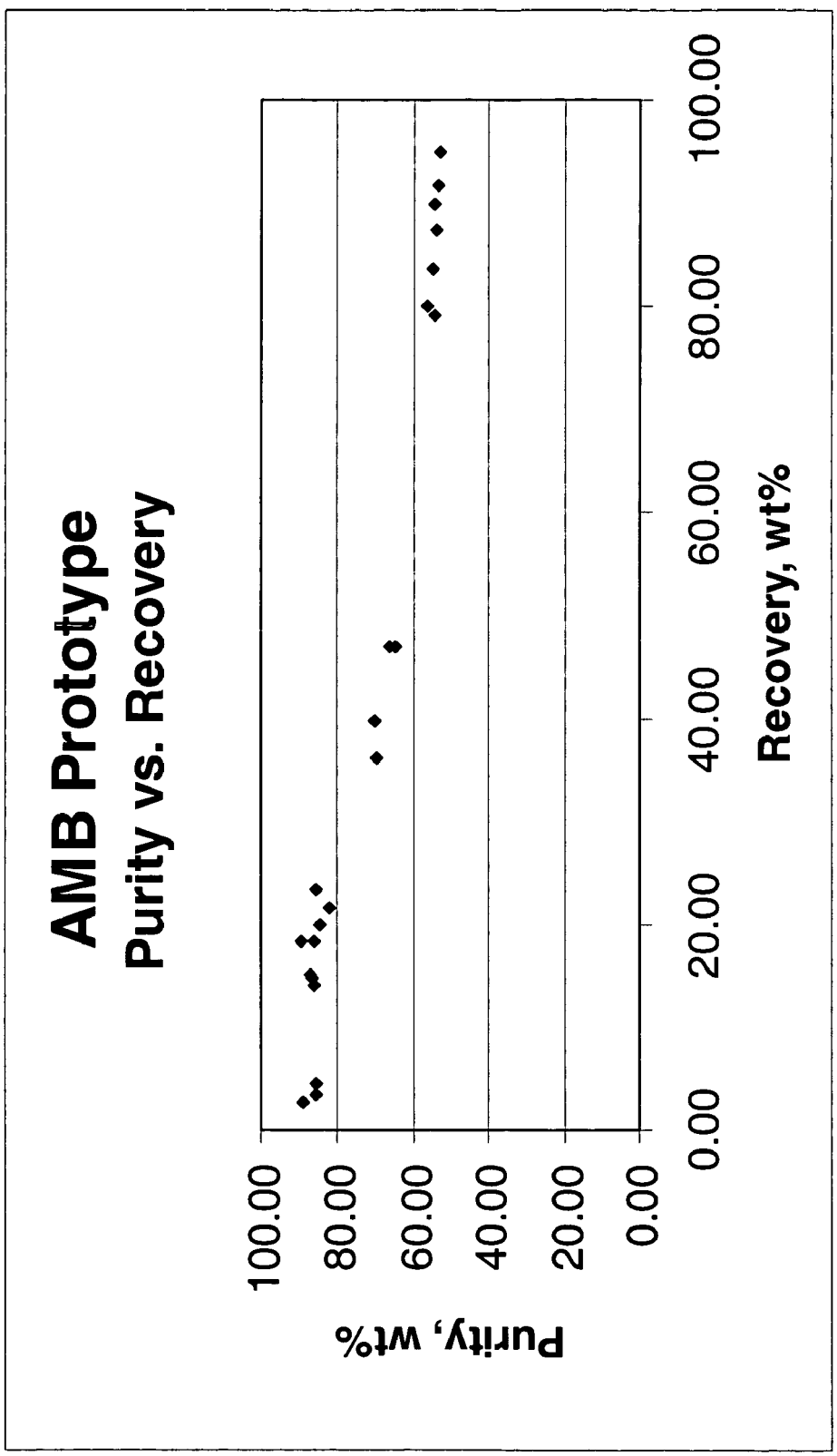
FIG. 11 is a plot of purity vs. recovery for a test case.

The apparatus was built and tested to verify the model design. A 50—50 mixture of glucose and fructose was chosen as a feed, and an adsorbent that preferentially adsorbed the fructose was used. The apparatus was operated at room temperature and deionized water was used as a desorbent. A plot of the purity vs. recovery is shown for the extract (fructose) in FIG. 11.

The actual moving bed system is especially useful for the extraction and purification of more than one component from a feedstream or for the extraction of a component in a mixture having intermediate adsorptive properties relative to other components in the mixture. In one embodiment, the invention comprises a plurality of desorbent feeds, a plurality of extract drawoffs, and a plurality of raffinate drawoffs. This embodiment provides for separating more than one component from a feed mixture. The invention, as described above, is the same with respect to the moving bed assembly including the spool 10 with the adsorbent beds, the bottom plate assembly 14, and the top plate assembly 44. The stator plate assembly includes a plurality of desorbent net flow lines, a plurality of raffinate net flow lines, and a plurality of extract net flow lines.

A feedstream comprising a mixture flows into an adsorption bed, and the adsorbent in the adsorbent bed selectively adsorbs at least two components from the feedstream. The solid adsorbent may adsorb two or more components or the solid adsorbent in the adsorbent bed may comprise a mixture of solid adsorbents with each adsorbent chosen to selectively adsorb one particular component from the mixture. The non-adsorbed components continue to move downstream and leave the apparatus through a first raffinate outflow. As the adsorbent beds are moved, countercurrent to the flow of liquid, the adsorbent beds pass through a purification zone where the adsorbed components and non-absorbed components are further separated.

The adsorbent beds continue to move countercurrent to the fluid flow to a first desorption zone. In this first desorption zone, one of the adsorbed components is preferentially displaced by a desorbent. The fluid carrying the desorbent and the preferentially desorbed component exits the apparatus through a first extract net flow port. After the first desorbent inlet the adsorbent beds move to a second purification zone where there is further separation of the preferentially desorbed component and a remaining adsorbed component.

The adsorbent beds continue to move countercurrent to the fluid flow to a second desorption zone. In the second desorption zone, the remaining adsorbed component is desorbed. The second desorption zone may use a second desorbent that preferentially desorbs the remaining component and the stream containing the remaining component exits through a second extract net flow port.

Figure 12:
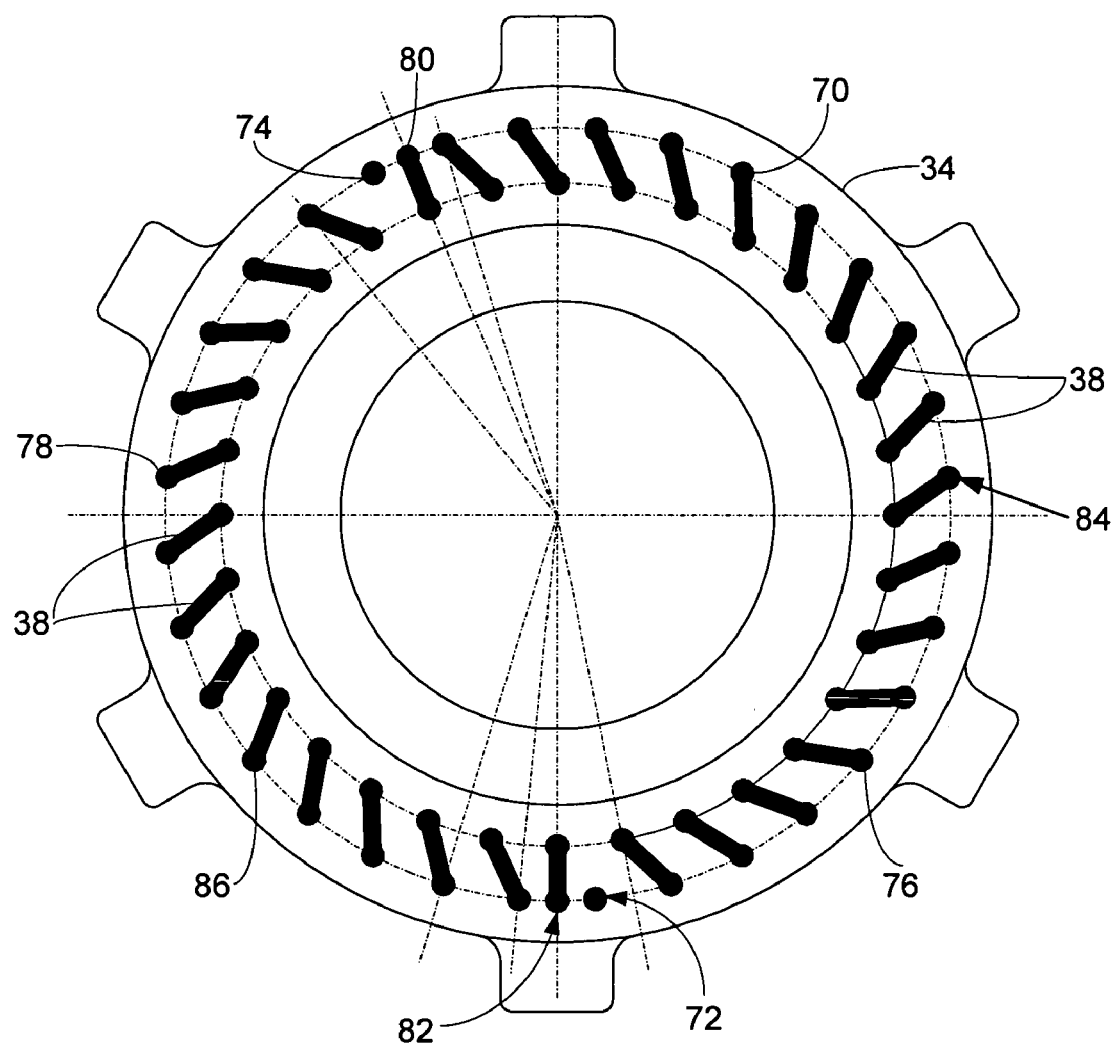
FIG. 12 is a bottom view of the second stator plate for design with multiple extracts.

In an alternate embodiment for multi component separation, the adsorbent beds, and the bottom plate assembly are as described above. The stator plate assembly includes a second stator plate 34 as shown in FIG. 12. The second stator plate comprises a mixture feed inlet port 70, two desorbent inlet ports 72, 74, two extract outlet ports 76, 78, two raffinate outlet ports 80, 82, an intermediate mixture outlet port 84 and an intermediate mixture inlet port 86. In this embodiment the stator plate assembly divides the apparatus into two adsorption-separation zone with the adsorbent bed traveling between the two zones. The second stator plate 34 also has one fewer cross-over channel than is described in an embodiment for a single component separation.

In the first adsorption zone, there is a first desorbent inlet port 72 for admitting a desorbent, a first extract port 76 for drawing off a first extract stream, a mixture feed port 70 for admitting a feed mixture to be separated, and a first raffinate port 80 for drawing off a stream of non-adsorbed components from the feed mixture, in the respective sequence. In addition to this sequence, there is an additional intermediate fluid outflow port 84 disposed between the first extract port 76 and mixture feed inlet port 70. This intermediate outflow port 84 receives an outflow stream including two or more adsorbed components, but with one of the components having a greater concentration than other components. This intermediate outflow stream is to be an intermediate feedstream for the second adsorption-separation zone.

In the second adsorption-separation zone, there is a second desorbent inlet port 74 for admitting a desorbent, a second extract port 78 for drawing off a second extract stream, a feed port 86 for admitting the intermediate outflow stream, and a second raffinate port 82 in the respective sequence. As can be seen in this specific embodiment, many of the net flow ports are intermediate ports and are in fluid communication with the cross-over channels 38.

The apparatus provides for the separation of a mixture into three process streams, a process stream of strongly adsorbed components that is recovered from the extract process streams, a process stream of relatively more weakly adsorbed components that is recovered in the second raffinate stream, and a stream of relatively non-adsorbed components that is recovered in the first raffinate stream. The intermediate outflow port 84 allows for drawing off a stream having a moderate separation of the intermediate adsorbed components. This stream is further purified when directed as a feed stream to the second adsorption-separation zone.

A benefit and flexibility of this apparatus is the basic design for the rotating spool 10, bottom plate assembly 14, and top plate assembly 44 remain unchanged for many separation processes. The second stator plate 34 can be changed for different adsorption-separation processes, thereby providing numerous capabilities with only changes to the second stator plate 34.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A miniature actual moving bed apparatus for the separation of components from a mixture comprising:
    a generally cylindrical spool defining a plurality of adsorbent bed channels, wherein each adsorbent bed channel holds a bed of adsorbent material;
    a bottom plate assembly having connecting channels defined in the plate assembly, affixed to the spool, and providing fluid communication between pairs of adsorbent bed channels;
    a stator plate assembly having cross channels defined in the plate assembly providing fluid communication between adsorbent bed channels, and a plurality of ports providing fluid communication with net flow lines; and
    means for rotating the spool and bottom plate assembly.

2. The apparatus of claim 1 wherein the cylindrical spool has a toroidal shape and the adsorbent bed channels are defined in the annular region.

3. The apparatus of claim 1 wherein the cylindrical spool is comprised of an impermeable material that does not have an affinity for adsorbing components from the mixture.

4. The apparatus of claim 1 further comprising adsorbent material disposed within the adsorbent bed channels.

5. The apparatus of claim 1 wherein the means for rotating the spool and bottom plate assembly is selected from the group consisting of a direct gear drive, a chain and gear drive, a belt drive, and a direct drive shaft affixed to the bottom plate assembly.

6. The apparatus of claim 1 wherein the stator plate assembly includes a plurality of plates, comprising;
   a first stator plate having a plurality of ports extending through the first stator plate and equal to the number of adsorbent bed channels; and
   a second stator plate defining a plurality of crossover channels for providing fluid communication between pairs of adsorbent bed channels.

7. The apparatus of claim 6 wherein the first stator plate further includes smear channels defined in the first stator plate.

8. The apparatus of claim 6 wherein the first stator plate is comprised of a lubricious polymeric material.

9. The apparatus of claim 1 wherein the bottom plate assembly includes a plurality of plates, comprising:
   a first bottom plate having a plurality of ports extending through the first bottom plate, and equal to the number of adsorbent bed channels; and
   a second bottom plate defining a plurality of connecting channels providing fluid communication between pairs of first bottom plate ports and pairs of adsorbent bed channels.

10. The apparatus of claim 1 further comprising a top plate assembly affixed to the spool and having ports in fluid communication with the adsorbent bed channels.

11. The apparatus of claim 10 wherein the top plate assembly further includes smear channels defined in the top plate assembly.

12. The apparatus of claim 10 wherein the top plate is comprised of a lubricious polymeric material.

13. The apparatus of claim 1 further comprising a housing for holding the apparatus, and providing a base to hold a shaft extending through the spool and bottom plate assembly, and around which the spool and bottom plate assembly rotate.

14. The apparatus of claim 1 further comprising means for pressing the spool, the bottom plate assembly, and the stator plate assembly together.

15. A miniature actual moving bed apparatus for the separation of components from a mixture comprising:
   a generally cylindrical spool defining a plurality of adsorbent bed channels, wherein each adsorbent bed channel holds a bed of adsorbent material;
   a bottom plate assembly having connecting channels defined in the plate assembly and providing fluid communication between pairs of adsorbent bed channels; and
   a stator plate assembly having cross channels defined in the plate assembly providing fluid communication between adsorbent bed channels, and having a plurality of ports for desorbent inflows, at least one raffinate net outflow port, at least one mixture feed inflow port, and at least one extract net outflow port.

16. The apparatus of claim 15 further comprising means for rotating the spool and bottom plate assembly.

17. The apparatus of claim 15 wherein the stator plate assembly further comprises:
   a second feed port positioned downstream of a second desorbent port;
   a fluid outflow port downstream of a first desorbent port; and
   means for transferring fluid from the fluid outflow port to the second feed port.

18. The apparatus of claim 17 wherein the means comprises a pump.

19. The apparatus of claim 15 wherein the stator plate comprises:
   at least two raffinate outflow ports; and
   at least two extract outflow ports.

* * * * *